United States Patent [19]
Gallagher et al.

[11] Patent Number: 5,932,446
[45] Date of Patent: Aug. 3, 1999

[54] HMVAB41

[75] Inventors: Kathleen Theresa Gallagher, Willow Grove; Mark R Hurle, Norristown; Kristine Kay Kikly, Linfield, all of Pa.

[73] Assignee: SmithKline Beecham Corporation, Philadelphia, Pa.

[21] Appl. No.: 08/979,095

[22] Filed: Nov. 26, 1997

Related U.S. Application Data

[60] Provisional application No. 60/056,353, Aug. 18, 1997.
[51] Int. Cl.$^6$ .............................. C12N 5/10; C12N 15/12; C12N 15/63; C07H 21/00
[52] U.S. Cl. ...................... 435/69.1; 435/320.1; 435/325; 435/252.3; 435/254.11; 435/440; 536/23.1; 536/23.5
[58] Field of Search ................................ 435/69.1, 320.1, 435/455, 471, 440, 325, 252.3, 254.11; 536/23.1, 23.5

[56] References Cited

PUBLICATIONS

Human Genome Sciences Corporation EST # 1583776.

*Primary Examiner*—Bruce R. Campell
*Assistant Examiner*—Scott D. Priebe
*Attorney, Agent, or Firm*—Elizabeth J. Hecht; Ratner & Prestia; William T. King

[57] ABSTRACT

HMVAB41 polypeptides and polynucleotides and methods for producing such polypeptides by recombinant techniques are disclosed. Also disclosed are methods for utilizing HMVAB41 polypeptides and polynucleotides in the design of protocols for the treatment of cancer, inflammation, autoimmunity, allergy, asthma, rheumatoid arthritis, CNS inflammation, cerebellar degeneration, Alzheimer's disease, Parkison's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern bladness, and bacterial, fungal, protozoan and viral infections, among others, and diagnostic assays for such conditions.

12 Claims, No Drawings

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 2129 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
AAAATATCTG TTATTTAGAC TTTTTTTTTA AGTCTCCAGG TTGAGGAGGA CACAAATATA      60

TCCTCCTAAA CCTTCCAGTA AGCAAGCTGT GGCATCCAGA TGATCTCCTG GGTCATGGGG     120

GATAAGGCTA ATCTCCTAGG TGTCTGGCAG ACAGGACAGG CAAATTCCCA GAATGCCAAA     180

ATATACCATC TGCTGCTGTT TGGCATTGCC CTTAAGTCCA GAGTGTGGAG GCTGGGGGTG     240

GGTCTCTGGC TACAGGAGAA CTCCCCTGGC AAGGGAGGGG TGAAAGGACT GCCTGTTGAA     300

CCCCCCATCT ATCCCCGCAC TATGGCAAGA TTGAGAGGAA TGACTAGATC AGGGAATGGC     360

CCGAAAGAAA AATCCAAAAC CTCCCAACCC TGGACAAGGC CACAGCTTTG AGAAACCGAA     420

GCCTCTGCTT CCTTCTCTTT GGCTTTACTG CTTCTAGATG CAAATACACA GAGCTCTGAG     480

ATTTTGTGTG CTGGGAGGTG ATAACTGTTA ACCCTCTATT CCAATAGCAC AGAAATTTCT     540

CTTTGCCTCA GAAGTGGTTT CTCATAGATC TCAGATCTCT TTTCAGGAAA AAGAAAAACA     600

ACAACAATAA CAACACATTA ATGACTCTGA AAGAGTCAGA CACCATTAAT TCCATTATTG     660

GTGTCTGTGC CAAGTGAAAT GAACGTCAGC TCTTTTCCCA GATATGTTTC CTTCTTTTGC     720

CTCCTATAAT AAGAGATGAT TTTACTGTAA TAATATAAGA CTCATCAATT TGACTCCAAA     780

TAGCTTTCCT ATCAACAGGC TAAGTGTAAA ATACCAGGAT CATTATTCAG TTGAGAATAG     840

ATAGAACTAG GAAGTAGCCA TCAAAAAAGA ATGATGAGGT GCATTGTGGA TTTGGGGTGT     900

AACTTGGTAT CTAACATACA GCCAGAATCA CAGTCATAGC ACACTTAATA TTTTATCAGA     960

AACTTGCGTG AACAAGTTAA GAGGACTCTC AACTTAAAAA TGACACCAAT TGCAATGATC    1020

TTGTTAACAT TTGTGATGAA AATAATAGCA AAGTGACTTA GACAAATTAC AATAGCCCAT    1080

AAAAATAAGA TAAAGTTTAA TACAAAGTAA GATGATGTTA AAAGACTTGA AATAAAACAG    1140

ATATGTTAAG TAGGCAACAC ATAGGTAAGC ATATAAAAAC AAGAAGATAC CAGGATAGAG    1200

CTGTCATTTT TGTGGGAGCC TGTGATGTGG AAAACCAAGA TGCCTGGTGA GTATAATGGA    1260

TATGGAAACC CCCCTTGTAA TAATTCCACA GTTCCAAGGG GCCAAGGTCT CCAGGTTGAG    1320

TCACTATTGT AAACACACCC ATAGATGAAT CCACATGCCA TACCTCCTTG AGTAAGTGGG    1380
```

```
GACTCAAACT AGGTCTGTCA ATTGTTCCAG AAAATTAAGC ATCTAAATAA TTTAATGATA    1440

ATTTAAAAGA AGCACAATGA AATATTTCAA GGAATGTCAC ATACAAGATT CTGTACCTCT    1500

TCTGCTTTGG TTAGACTCAT TCAGAATAGG TTCCTGCTTT GATCTTAAGA GGGAGGTAGA    1560

GATTCTGGAG AAGCCCTAGG GAAGAGCAAA AGGAAAGGAA TAAGGAGCCA AGAGGAAACC    1620

CAGGGTAAGG CTGAGGAGGG ACTGTTTCGT GTAGGTGATT TATTGGAAGG GTTGGAAGGA    1680

AACATGGAAT GACAATTACC TTTGGTTATT GTCAGGTTAG TATGAGACTT ACAAGAAAAG    1740

CACTGCTCAG ACGCAATTAC CATTCAAGAT AAGAAATAAG AGGAAAGGCT AGCACACTTA    1800

GCTTTTTATT TAAAAAAGTG TTAGGTAGGC TGAGCACGGT GGCTCACTCC TGTAATCCCA    1860

GCACTTTGGG AGGCCAAGGT GGATAGATGA CTTGAGCCCA GAAGCTTGAG ACCAGCCTGG    1920

ACAACATGGT GAAACCTCAT GTTTACAAAA AAATACAAAA ATTAGCCAGG CATGATGGCA    1980

TGCACCTGTA GTCTCAGTTA CTTGGGGGGC CAAGAGGTGG GAAGATTGCT TGAGCCCAGG    2040

AAGTCGAGGC TGCAGTGAGC CATGATTGTG CCACTGCATG ACAGCCTGGG CAACCGAGTG    2100

AGAGCCTGCC TCAAAAAAAA AAAAAAAA                                        2129

(2) INFORMATION FOR SEQ ID NO:2:

(i) SEQUENCE CHARACTERISTICS:
        (A) LENGTH: 103 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Ile Ser Trp Val Met Gly Asp Lys Ala Asn Leu Leu Gly Val Trp
1               5                   10                  15

Gln Thr Gly Gln Ala Asn Ser Gln Asn Ala Lys Ile Tyr His Leu Leu
            20                  25                  30

Leu Phe Gly Ile Ala Leu Lys Ser Arg Val Trp Arg Leu Gly Val Gly
        35                  40                  45

Leu Trp Leu Gln Glu Asn Ser Pro Gly Lys Gly Val Lys Gly Leu
    50                  55                  60

Pro Val Glu Pro Pro Ile Tyr Pro Arg Thr Met Ala Arg Leu Arg Gly
65                  70                  75                  80

Met Thr Arg Ser Gly Asn Gly Pro Lys Glu Lys Ser Lys Thr Ser Gln
                85                  90                  95

Pro Trp Thr Arg Pro Gln Leu
            100

(2) INFORMATION FOR SEQ ID NO:3:

(i) SEQUENCE CHARACTERISTICS:
        (A) LENGTH: 2076 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

AAATATATCC TCCTAAACCT TCCAGTAAGC AAGCTGTGGC ATCCAGATGA TCTCCTGGGT      60

CATGGGGGAT AAGGCTAATC TCCTAGGTGT CTGGCAGACA GGACAGGCAA ATTCCCAGAA     120

TGCCAAAATA TACCATCTGC TGCTGTTTGG CATTGCCCTT AAGTCCAGAG TGTGGAGGCT     180
```

```
GGGGGTGGGT CTCTGGCTAC AGGAGAACTC CCCTGGCAAG GGAGGGGTGA AAGGACTGCC      240

TGTTGAACCC CCCATCTATC CCCGCACTAT GGCAAGATTG AGAGGAATGA CTAGATCAGG      300

GAATGGCCCG AAAGAAAAAT CCAAAACCTC CCAACCCTGG ACAAGGCCAC AGCTTTGAGA      360

AACCGAAGCC TCTGCTTCCT TCTCTTTGGC TTTACTGCTT CTAGATGCAA ATACACAGAG      420

CTCTGAGATT TTGTGTGCTG GGAGGTGATA ACTGTTAACC CTCTATTCCA ATAGCACAGA      480

AATTTCTCTT TGCCTCAGAA GTGGTTTCTC ATAGATCTCA GATCTCTTTT CAGGAAAAAG      540

AAAAACAACA ACAATAACAA CACATTAATG ACTCTGAAAG AGTCAGACAC CATTAATTCC      600

ATTATTGGTG TCTGTGCCAA GTGAAATGAA CGTCAGCTCT TTTCCCAGAT ATGTTTCCTT      660

CTTTTGCCTC CTATAATAAG AGATGATTTT ACTGTAATAA TATAAGACTC ATCAATTTGA      720

CTCCAAATAG CTTTCCTATC AACAGGCTAA GTGTAAAATA CCAGGATCAT TATTCAGTTG      780

AGAATAGATA GAACTAGGAA GTAGCCATCA AAAAAGAATG ATGAGGTGCA TTGTGGATTT      840

GGGGTGTAAC TTGGTATCTA ACATACAGCC AGAATCACAG TCATAGCACA CTTAATATTT      900

TATCAGAAAC TTGCGTGAAC AAGTTAAGAG GACTCTCAAC TTAAAAATGA CACCAATTGC      960

AATGATCTTG TTAACATTTG TGATGAAAAT AATAGCAAAG TGACTTAGAC AAATTACAAT     1020

AGCCCATAAA AATAAGATAA AGTTTAATAC AAAGTAAGAT GATGTTAAAA GACTTGAAAT     1080

AAAACAGATA TGTTAAGTAG GCAACACATA GGTAAGCATA TAAAAACAAG AAGATACCAG     1140

GATAGAGCTG TCATTTTTGT GGGAGCCTGT GATGTGGAAA ACCAAGATGC CTGGTGAGTA     1200

TAATGGATAT GGAAACCCCC CTTGTAATAA TTCCACAGTT CCAAGGGGCC AAGGTCTCCA     1260

GGTTGAGTCA CTATTGTAAA CACACCCATA GATGAATCCA CATGCCATAC CTCCTTGAGT     1320

AAGTGGGGAC TCAAACTAGG TCTGTCAATT GTTCCAGAAA ATTAAGCATC TAAATAATTT     1380

AATGATAATT TAAAAGAAGC ACAATGAAAT ATTTCAAGGA ATGTCACATA CAAGATTCTG     1440

TACCTCTTCT GCTTTGGTTA GACTCATTCA GAATAGGTTC CTGCTTTGAT CTTAAGAGGG     1500

AGGTAGAGAT TCTGGAGAAG CCCTAGGGAA GAGCAAAAGG AAAGGAATAA GGAGCCAAGA     1560

GGAAACCCAG GGTAAGGCTG AGGAGGGACT GTTTCGTGTA GGTGATTTAT TGGAAGGGTT     1620

GGAAGGAAAC ATGGAATGAC AATTACCTTT GGTTATTGTC AGGTTAGTAT GAGACTTACA     1680

AGAAAAGCAC TGCTCAGACG CAATTACCAT TCAAGATAAA AAATAAGAGG AAAGGCTAGC     1740

ACACTTAGCT TTTTATTTAA AAAAGTGTTA GGTAGGCTGA GCACGGTGGC TCACTCCTGT     1800

AATCCCAGCA CTTTGGGAGG CCAAGGTGGA TAGATGACTT GAGCCCAGAA GCTTGAGACC     1860

AGCCTGGACA ACATGGTGAA ACCTCATGTT TACAAAAAAA TACAAAAATT AGCCAGGCAT     1920

GATGGCATGC ACCTGTAGTC TCAGTTACTT GGGGGGCCAA GAGGTGGGAA GATTGCTTGA     1980

GCCCAGGAAG TCGAGGCTGC AGTGAGCCAT GATTGTGCCA CTGCATGACA GCCTGGGCAA     2040

CCGAGTGAGA GCCTGCCTCA AAAAAAAAA AAAAAA                                2076
```

HMVAB41

This application claims the benefit of U.S. Provisional Application No. 60/056,353, filed Aug. 18, 1997.

FIELD OF INVENTION

This invention relates to newly identified polynucleotides, polypeptides encoded by them and to the use of such polynucleotides and polypeptides, and to their production, hereinafter referred to as HMVAB41. The invention also relates to inhibiting or activating the action of such polynucleotides and polypeptides.

BACKGROUND OF THE INVENTION

The drug discovery process is currently undergoing a fundamental revolution as it embraces 'functional genomics', that is, high throughput genome- or gene-based biology. This approach is rapidly superceding earlier approaches based on 'positional cloning'. A phenotype, that is a biological function or genetic disease, would be identified and this would then be tracked back to the responsible gene, based on its genetic map position. Functional genomics relies heavily on the various tools of bioinformatics to identify gene sequences of potential interest from the many molecular biology databases now available. There is a continuing need to identify and characterise further genes and their related polypeptides/proteins, as targets for drug discovery.

This indicates that HMVAB41 related genes have an established, proven history as therapeutic targets. Clearly there is a need for identification and characterization of further members of this family which can play a role in preventing, ameliorating or correcting dysfunctions or diseases, including, but not limited to, cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections.

SUMMARY OF THE INVENTION

In one aspect, the invention relates to HMVAB41 polypeptides and recombinant materials and methods for their production. Another aspect of the invention relates to methods for using such HMVAB41 polypeptides and polynucleotides. Such uses include the treatment of cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections, among others. In still another aspect, the invention relates to methods to identify agonists and antagonists using the materials provided by the invention, and treating conditions associated with HMVAB41 imbalance with the identified compounds. Yet another aspect of the invention relates to diagnostic assays for detecting diseases associated with inappropriate HMVAB41 activity or levels.

DESCRIPTION OF THE INVENTION

Definitions

The following definitions are provided to facilitate understanding of certain terms used frequently herein.

"HMVAB41" refers, among others, generally to a polypeptide having the amino acid sequence set forth in SEQ ID NO:2 or an allelic variant thereof.

"HMVAB41 activity or HMVAB41 polypeptide activity" or "biological activity of the HMVAB41 or HMVAB41 polypeptide" refers to the metabolic or physiologic function of said HMVAB41 including similar activities or improved activities or these activities with decreased undesirable side-effects. Also included are antigenic and immunogenic activities of said HMVAB41.

"HMVAB41 gene" refers to a polynucleotide having the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS - STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Posttranslational Modifications and Aging", Ann NY Acad Sci (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Hleinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., SIAM J Applied Math (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., SIAM J Applied Math (1988) 48:1073. Methods to determine identity and similarity are codified in computer programs. Preferred computer program methods to determine identity and similarity between two sequences include, but are not limited to, GCS program package (Devereux, J., et al., Nucleic Acids Research (1984) 12(1):387), BLASTP, BLASTN, FASTA (Atschul, S. F. et al., J Molec Biol (1990) 215:403).

As an illustration, by a polynucleotide having a nucleotide sequence having at least, for example, 95% "identity" to a reference nucleotide sequence of SEQ ID NO:1 is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to HMVAB41 polypeptides (or HMVAB41 proteins). The HMVAB41 polypeptides include the polypeptide of SEQ ID NO:2; as well as polypeptides comprising the amino acid sequence of SEQ ID NO:2; and polypeptides comprising the amino acid sequence which have at least 80% identity to that of SEQ ED NO:2 over its entire length, and still more preferably at least 90% identity, and even still more preferably at least 95% identity to SEQ ID NO:2. Furthermore, those with at least 97–99% are highly preferred. Also included within HMVAB41 polypeptides are polypeptides having the amino acid sequence which have at least 80% identity to the polypeptide having the amino acid sequence of SEQ ID NO:2 over its entire length, and still more preferably at least 90% identity, and still more preferably at least 95% identity to SEQ ID NO:2. Furthermore, those with at least 97–99% are highly preferred. Preferably HMVAB41 polypeptide exhibit at least one biological activity of HMVAB41.

The HMVAB41 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the HMVAB41 polypeptides are also included in the invention. A fragment is a polypeptide having an amino acid sequence that entirely is the same as part, but not all, of the amino acid sequence of the aforementioned HMVAB41 polypeptides. As with HMVAB41 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of HMVAB41 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of HMVAB41 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophobic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate HMVAB41 activity, including those with a similar activity or an improved activity, or with a decreased undesirable activity. Also included are those that are antigenic or immunogenic in an animal, especially in a human.

Preferably, all of these polypeptide fragments retain the biological activity of the HMVAB41, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The HMVAB41 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to HMVAB41 polynucleotides. HMVAB41 polynucleotides include isolated polynucleotides which encode the HMVAB41 polypeptides and fragments, and polynucleotides closely related thereto. More specifically, HMVAB41 polynucleotide of the invention include a polynucleotide comprising the nucleotide sequence contained in SEQ ID NO:1 encoding a HMVAB41 polypeptide of SEQ ID NO:2, and polynucleotides having the particular sequences of SEQ ID NOS:1 and 3. HMVAB41 polynucleotides further include a polynucleotide comprising a nucleotide sequence that has at least 80% identity over its entire length to a nucleotide sequence encoding the HMVAB41 polypeptide of SEQ ID NO:2, and a polynucleotide comprising a nucleotide sequence that is at least 80% identical to that of SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under HMVAB41 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such HMVAB41 polynucleotides.

The cDNA sequence of SEQ ID NO:1 contains an open reading frame (nucleotide number 100 to 408) encodiing a polypeptide of 103 amino acids of SEQ ID NO:2. Thus HMVAB41 polypeptides and polynucleotides of the present invention are expected to have, inter alia, similar biological functions/properties to their homologous polypeptides and polynucleotides, and their utility is obvious to anyone skilled in the art.

TABLE 1ᵃ

| | |
|---|---|
| 1 | AAAATATCTG TTATTTAGAC TTTTTTTTTA AGTCTCCAGG TTGAGGAGGA |
| 51 | CACAAATATA TCCTCCTAAA CCTTCCAGTA AGCAAGCTGT GGCATCCAGA |
| 101 | TGATCTCCTG GGTCATGGGG GATAAGGCTA ATCTCCTAGG TGTCTGGCAG |
| 151 | ACAGGACAGG CAAATTCCCA GAATGCCAAA ATATACCATC TGCTGCTGTT |
| 201 | TGGCATTGCC CTTAAGTCCA GAGTGTGGAG GCTGGGGGTG GGTCTCTGGC |
| 251 | TACAGGAGAA CTCCCCTGGC AAGGGAGGGG TGAAAGGACT GCCTGTTGAA |
| 301 | CCCCCCATCT ATCCCCGCAC TATGGCAAGA TTGAGAGGAA TGACTAGATC |
| 351 | AGGGAATGGC CCGAAAGAAA AATCCAAAAC CTCCCAACCC TGGACAAGGC |
| 401 | CACAGCTTTG AGAAACCGAA GCCTCTGCTT CCTTCTCTTT GGCTTTACTG |
| 451 | CTTCTAGATG CAAATACACA GAGCTCTGAG ATTTTGTGTG CTGGGAGGTG |
| 501 | ATAACTGTTA ACCCTCTATT CCAATAGCAC AGAAATTTCT CTTTGCCTCA |
| 551 | GAAGTGGTTT CTCATAGATC TCAGATCTCT TTTCAGGAAA AAGAAAAACA |
| 601 | ACAACAATAA CAACACATTA ATGACTCTGA AAGAGTCAGA CACCATTAAT |
| 651 | TCCATTATTG GTGTCTGTGC CAAGTGAAAT GAACGTCAGC TCTTTTCCCA |
| 701 | GATATGTTTC CTTCTTTTGC CTCCTATAAT AAGAGATGAT TTTACTGTAA |
| 751 | TAATATAAGA CTCATCAATT TGACTCCAAA TAGCTTTCCT ATCAACAGGC |
| 801 | TAAGTGTAAA ATACCAGGAT CATTATTCAG TTGAGAATAG ATAGAACTAG |
| 851 | GAAGTAGCCA TCAAAAAAGA ATGATGAGGT GCATTGTGGA TTTGGGGTGT |
| 901 | AACTTGGTAT CTAACATACA GCCAGAATCA CAGTCATAGC ACACTTAATA |
| 951 | TTTTATCAGA AACTTGCGTG AACAAGTTAA GAGGACTCTC AACTTAAAAA |
| 1001 | TGACACCAAT TGCAATGATC TTGTTAACAT TTGTGATGAA AATaATAGCA |
| 1051 | AAGTGACTTA GACAAATTAC aATAGCCCAT AAAAATAAGA TAAAGTTtAA |
| 1101 | TACAAAGTAA GATGATGTtA AAAGACtTGA AATAAAACAG ATATGtTAAG |
| 1151 | TAGGCAACAC ATAGGTAaGC ATATAAAAAC AaGAAGATAC CAGGATAGAG |
| 1201 | CTGTCATTTT TGTGGGAGCC TGTGATGTGG AAAACCAAGA TGCCTGGTGA |
| 1251 | GTATAATGGA TATGGAAACC CCCCTTGTAA TAATTCCACA GTTCCAAGGG |
| 1301 | GCCAAGGTCT CCAGGTTGAG TCACTATTGT AAACACACCC ATAGATGAAT |
| 1351 | CCACATGCCA TACCTCCTTG AGTAAGTGGG GACTCAAACT AGGTCTGTCA |
| 1401 | ATTGTTCCAG AAAATTAAGC ATCTAAATAA TTTAATGATA ATTTAAAAGA |
| 1451 | AGCACAATGA AATATTTCAA GGAATGTCAC ATACAAGATT CTGTACCTCT |
| 1501 | TCTGCTTTGG TTAGACTCAT TCAGAATAGG TTCCTGCTTT GATCTTAAGA |
| 1551 | GGGAGGTAGA GATTCTGGAG AAGCCCTAGG GAAGAGCAAA AGGAAAGGAA |
| 1601 | TAAGGAGCCA AGAGGAAACC CAGGGTAAGG CTGAGGAGGG ACTGTTTCGT |
| 1651 | GTAGGTGATT TATTGGAAGG GTTGGAAGGA AACATGGAAT GACAATTACC |

TABLE 1ᵃ-continued

| | | | | |
|---|---|---|---|---|
| 1701 | TTTGGTTATT | GTCAGGTTAG | TATGAGACTT | ACAAGAAAAG CACTGCTCAG |
| 1751 | ACGCAATTAC | CATTCAAGAT | AAGAAATAAG | AGGAAAGGCT AGCACACTTA |
| 1801 | GCTTTTTATT | TAAAAAAGTG | TTAGGTAGGC | TGAGCACGGT GGCTCACTCC |
| 1851 | TGTAATCCCA | GCACTTTGGG | AGGCCAAGGT | GGATAGATGA CTTGAGCCCA |
| 1901 | GAAGCTTGAG | ACCAGCCTGG | ACAACATGGT | GAAACCTCAT GTTTACAAAA |
| 1951 | AAATACAAAA | ATTAGCCAGG | CATGATGGCA | TGCACCTGTA GTCTCAGTTA |
| 2001 | CTTGGGGGGC | CAAGAGGTGG | GAAGATTGCT | TGAGCCCAGG AAGTCGAGGC |
| 2051 | TGCAGTGAGC | CATGATTGTG | CCACTGCATG | ACAGCCTGGG CAACCGAGTG |
| 2101 | AGAGCCTGCC | TCAAAAAAAA | AAAAAAAA | |

ᵃA nucleotide sequence of a human HMVAB41 (SEQ ID0 NO: 1).

TABLE 2ᵇ

| | |
|---|---|
| 1 | MISWVMGDKA NLLGVWQTGQ ANSQNAKIYH LLLFGIALKS RVWRLGVGLW |
| 51 | LQENSPGKGG VKGLPVEPPI YPRTMARLRG MTRSGNGPKE KSKTSQPWTR |
| 101 | PQL. |

ᵇAn amino acid sequence of a human HMVAB41 (SEQ ID NO: 2).

One polynucleotide of the present invention encoding HMVAB41 may be obtained using standard cloning and screening, from a cDNA library derived from mRNA in cells of human bone marrow stroma using the expressed sequence tag (EST) analysis (Adams, M. D., et al Science (1991) 252:1651–1656; Adams, M. D. et al., Nature, (1992) 355:632–634; Adams, M. D., et al., Nature (1995) 377 Supp:3–174). Polynucleotides of the invention can also be obtained from natural sources such as genomic DNA libraries or can be synthesized using well known and commercially available techniques.

The nucleotide sequence encoding HMVAB41 polypeptide of SEQ ID NO:2 may be identical to the polypeptide encoding sequence contained in Table 1 (nucleotide number 100 to 408 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of HMVAB41 polypeptide, the polynucleotide may include the coding sequence for the mature polypeptide or a fragment thereof, by itself, the coding sequence for the mature polypeptide or fragment in reading frame with other coding sequences, such as those encoding a leader or secretory sequence, a pre-, or preproprotein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain bonding 5' and 3' sequences, such as transcribed, non-translated sequences, splicing and polyadenylation signals, ribosome binding sites and sequences that stabilize mRNA.

Further preferred embodiments are polynucleotides encoding HMVAB41 variants comprising the amino acid sequence of HMVAB41 polypeptide of Table 2 (SEQ ID NO:2) in which several, 5–10, 1–5, 1–3, 1–2 or 1 amino acid residues are substituted, deleted or added, in any combination. Among the preferred nucleotides of the present invention is contained in Table 3 (SEQ ID NO:3).

TABLE 3ᶜ

```
   1  AAATATATCC TCCTAAACCT TCCAGTAAGC AAGCTGTGGC ATCCAGATGA
  51  TCTCCTGGGT CATGGGGGAT AAGGCTAATC TCCTAGGTGT CTGGCAGACA
 101  GGACAGGCAA ATTCCCAGAA TGCCAAAATA TACCATCTGC TGCTGTTTGG
 151  CATTGCCCTT AAGTCCAGAG TGTGGAGGCT GGGGGTGGGT CTCTGGCTAC
 201  AGGAGAACTC CCCTGGCAAG GGAGGGGTGA AAGGACTGCC TGTTGAACCC
 251  CCCATCTATC CCCGCACTAT GGCAAGATTG AGAGGAATGA CTAGATCAGG
 301  GAATGGCCCG AAAGAAAAAT CCAAAACCTC CCAACCCTGG ACAAGGCCAC
 351  AGCTTTGAGA AACCGAAGCC TCTGCTTCCT TCTCTTTGGC TTTACTGCTT
 401  CTAGATGCAA ATACACAGAG CTCTGAGATT TTGTGTGCTG GGAGGTGATA
 451  ACTGTTAACC CTCTATTCCA ATAGCACAGA AATTTCTCTT TGCCTCAGAA
 501  GTGGTTTCTC ATAGATCTCA GATCTCTTTT CAGGAAAAAG AAAAACAACA
 551  ACAATAACAA CACATTAATG ACTCTGAAAG AGTCAGACAC CATTAATTCC
 601  ATTATTGGTG TCTGTGCCAA GTGAAATGAA CGTCAGCTCT TTTCCCAGAT
 651  ATGTTTCCTT CTTTTGCCTC CTATAATAAG AGATGATTTT ACTGTAATAA
 701  TATAAGACTC ATCAATTTGA CTCCAAATAG CTTTCCTATC AACAGGCTAA
 751  GTGTAAAATA CCAGGATCAT TATTCAGTTG AGAATAGATA GAACTAGGAA
 801  GTAGCCATCA AAAAGAATG ATGAGGTGCA TTGTGGATTT GGGGTGTAAC
 851  TTGGTATCTA ACATACAGCC AGAATCACAG TCATAGCACA CTTAATATTT
 901  TATCAGAAAC TTGCGTGAAC AAGTTAAGAG GACTCTCAAC TTAAAAATGA
 951  CACCAATTGC AATGATCTTG TTAACATTTG TGATGAAAAT aATAGCAAAG
1001  TGACTTAGAC AAATTACaAT AGCCCATAAA AATAAGATAA AGTTtAATAC
1051  AAAGTAAGAT GATGTtAAAA GACtTGAAAT AAAACAGATA TGtTAAGTAG
1101  GCAACACATA GGTAaGCATA TAAAAACAaG AAGATACCAG GATAGAGCTG
1151  TCATTTTTGT GGGAGCCTGT GATGTGGAAA ACCAAGATGC CTGGTGAGTA
1201  TAATGGATAT GGAAACCCCC CTTGTAATAA TTCCACAGTT CCAAGGGGCC
1251  AAGGTCTCCA GGTTGAGTCA CTATTGTAAA CACACCCATA GATGAATCCA
1301  CATGCCATAC CTCCTTGAGT AAGTGGGGAC TCAAACTAGG TCTGTCAATT
1351  GTTCCAGAAA ATTAAGCATC TAAATAATTT AATGATAATT TAAAAGAAGC
1401  ACAATGAAAT ATTTCAAGGA ATGTCACATA CAAGATTCTG TACCTCTTCT
1451  GCTTTGGTTA GACTCATTCA GAATAGGTTC CTGCTTTGAT CTTAAGAGGG
1501  AGGTAGAGAT TCTGGAGAAG CCCTAGGGAA GAGCAAAAGG AAAGGAATAA
1551  GGAGCCAAGA GGAAACCCAG GGTAAGGCTG AGGAGGGACT GTTTCGTGTA
1601  GGTGATTTAT TGGAAGGGTT GGAAGGAAAC ATGGAATGAC AATTACCTTT
1651  GGTTATTGTC AGGTTAGTAT GAGACTTACA AGAAAAGCAC TGCTCAGACG
1701  CAATTACCAT TCAAGATAAG AAATAAGAGG AAAGGCTAGC ACACTTAGCT
1751  TTTTATTTAA AAAAGTGTTA GGTAGGCTGA GCACGGTGGC TCACTCCTGT
1801  AATCCCAGCA CTTTGGGAGG CCAAGGTGGA TAGATGACTT GAGCCCAGAA
1851  GCTTGAGACC AGCCTGGACA ACATGGTGAA ACCTCATGTT TACAAAAAAA
```

TABLE 3ᶜ-continued

```
1901    TACAAAAATT AGCCAGGCAT GATGGCATGC ACCTGTAGTC TCAGTTACTT

1951    GGGGGGCCAA GAGGTGGGAA GATTGCTTGA GCCCAGGAAG TCGAGGCTGC

2001    AGTGAGCCAT GATTGTGCCA CTGCATGACA GCCTGGGCAA CCGAGTGAGA

2051    GCCTGCCTCA AAAAAAAAAA AAAAAA
```

ᶜA partial nucleotide sequence of a human HMVAB41 (SEQ ID NO: 3).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof (including that of SEQ ID NO:3), may be used as hybridization probes for cDNA and genomic DNA, to isolate full-length cDNAs and genomic clones encoding HMVAB41 polypeptide and to isolate cDNA and genomic clones of other genes (including genes encoding homologs and orthologs from species other than human) that have a high sequence similarity to the HMVAB41 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding HMVAB41 polypeptide, including homologs and orthologs from species other than human, comprises the steps of screening an appropriate library under stringent hybridization conditions with a labeled probe having the SEQ ID NO:1 or a fragment thereof (including that of SEQ ID NO:3), and isolating full-length cDNA and genomic clones containing said polynucleotide sequence. Such hybridization techniques are well known to those of skill in the art. Thus in another aspect, HMVAB41 polynucleotides of the present invention further include a nucleotide sequence comprising a nucleotide sequence that hybridize under stringent condition to a nucleotide sequence having SEQ ID NO:1 or a fragment thereof (including that of SEQ ID NO:3). Also included with HMVAB41 polypeptides are polypeptide comprising amino acid sequence encoded by nucleotide sequence obtained by the above hybridization condition. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides a of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al, BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *streptococci, staphylococci, E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviuses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HMVAB41 polypeptide is to be expressed for use in screening assays, generally, it is preferred that the polypeptide be produced at the surface of the cell. In this event, the cells may be harvested prior to use in the screening assay. If HMVAB41 polypeptide is secreted into the medium, the medium can be recovered in order to recover and purify the polypeptide; if produced intracellularly, the cells must first be lysed before the polypeptide is recovered. HMVAB41 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of HMVAB41 polynucleotides for use as diagnostic reagents. Detection of a mutated form of HMVAB41 gene associated with a dysfunction will provide a diagnostic tool that can add to or define a diagnosis of a disease or susceptibility to a disease which results from under-expression, over-expression or altered expression of HMVAB41. Individuals carrying mutations in the HMVAB41 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be defined by a change in size of the amplified product in comparison to the normal genotype. Point mutations can be identified by hybridizing amplified DNA to labeled HMVAB41 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., Science (1985) 230:1242. Sequence changes at specific locations may also be revealed by nuclease protection assays, such as RNase and S1 protection or the chemical cleavage method. See Cotton et al., Proc Natl Acad Sci USA (1985) 85:4397–4401. In another embodiment, an array of oligonucleotides probes comprising HMVAB41 nucleotide sequence or fragments thereof can be constructed to conduct efficient screening of e.g., genetic mutations. Array technology methods are well known and have general applicability and can be used to address a variety of questions in molecular geneics including gene expression, genetic linkage, and genetic variability. (See for example: M. Chee et al., Science, Vol 274, pp 610–613 (1996)).

The diagnostic assays offer a process for diagnosing or determining a susceptibility to cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, arthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections through detection of mutation in the HMVAB41 gene by the methods described.

In addition, cancer, inflammation, autoimmunity, allergy, asthma rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections, can be diagnosed by methods comprising determining from a sample derived from a subject an abnormally decreased or increased level of HMVAB41 polypeptide or HMVAB41 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an HMVAB41 polypeptide, in a sample derived from a host are well-known to those of skill in the art. Such assay methods include radioimmunoassays, competitive-binding assays, Western Blot analysis and ELISA assays.

Thus in another aspect, the present invention relates to a diagonostic kit for a disease or suspectability to a disease, particularly cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections, which comprises:

(a) HMVAB41 polynucleotide, preferably the nucleotide sequence of SEQ ID NO:1, or a fragment thereof;
(b) nucleotide sequence complementary to that of (a);
(c) HMVAB41 polypeptide, preferably the polypeptide of SEQ ID NO:2, or a fragment thereof, or
(d) antibody to a HMVAB41 polypeptide, preferably to the polypeptide of SEQ ID NO:2.

It, will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the HMVAB41 polypeptides. The term "immunospecific" means that the antibodies have substantial greater affinity for the polypeptides of the invention than their affinity for other related polypeptides in the prior art.

Antibodies generated against the HMVAB41 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against HMVAB41 polypeptides may also be employed to treat cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections, among others.

Vaccines

Another aspect of the invention relates to a method for inducing an immunological response in a mammal which comprises inoculating the mammal with HMVAB41 polypeptide, or a fragment thereof, adequate to produce antibody and/or T cell immune response to protect said animal from cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections, among others. Yet another aspect of the invention relates to a method of inducing immunological response in a mammal which comprises, delivering HMVAB41 polypeptide via a vector directing expression of HMVAB41 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a HMVAB41 polypeptide wherein the composition comprises a HMVAB41 polypeptide or HMVAB41 gene. The vaccine formulation may further comprise a suitable carrier. Since HMVAB41 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immmunogenicity of the formulation, such as oil-in water systems and other systems known in the art. The dosage will depend on the specific activity of the vaccine and can be readily determined by routine experimentation.

Screening Assays

The HMVAB41 polypeptide of the present invention may be employed in a screening process for compounds which activate (agonists) or inhibit activation of (antagonists, or otherwise called inhibitors) the HMVAB41 polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, enzymes, receptors, etc., as the case may be, of the polypeptide of the present invention; or may be structural or functional mimetics of the polypeptide of the present invention. See Coligan et al., Current Protocols in Immunology 1(2):Chapter 5 (1991).

HMVAB41 polypeptides are responsible for many biological functions, including many pathologies. Accordingly, it is desirous to find compounds and drugs which stimulate HMVAB41 polypeptide on the one hand and which can inhibit the function of HMVAB41 polypeptide on the other hand. In general, agonists are employed for therapeutic and prophylactic purposes for such conditions as cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections. Antagonists may be employed for a variety of therapeutic and prophylactic purposes for such conditions as cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections.

In general, such screening procedures may involve using appropriate cells which express the HMVAB41 polypeptide or respond to HMVAB41 polypeptide of the present invention. Such cells include cells from mammals, yeast, *Drosophila* or *E. coli*. Cells which express the HMVAB41 polypeptide (or cell membrane containing the expressed polypeptide) or respond to HMVAB41 polypeptide are then contacted with a test compound to observe binding, or stimulation or inhibition of a functional response. The ability of the cells which were contacted with the candidate compounds is compared with the same cells which were not contacted for HMVAB41 activity.

The assays may simply test binding of a candidate compound wherein adherence to the cells bearing the HMVAB41 polypeptide is detected by means of a label directly or indirectly associated with the candidate compound or in an assay involving competition with a labeled competitor. Further, these assays may test whether the candidate compound results in a signal generated by activation of the HMVAB41 polypeptide, using detection systems appropriate to the cells bearing the HMVAB41 polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a HMVAB41 polypeptide to form a mixture, measuring HMVAB41 activity in the mixture, and comparing the HMVAB41 activity of the mixture to a standard.

The HMVAB41 cDNA, protein and antibodies to the protein may also be used to configure assays for detecting the effect of added compounds on the production of HMVAB41 mRNA and protein in cells. For example, an ELISA may be constructed for measuring secreted or cell associated levels of HMVAB41 protein using monoclonal and polyclonal antibodies by standard methods known in the art, and this can be used to discover agents which may inhibit or enhance the production of HMVAB41 (also called antagonist or agonist, respectively) from suitably manipulated cells or tissues.

The HMVAB41 protein may be used to identify membrane bound or soluble receptors, if any, through standard receptor binding techniques known in the art. These include, but are not limited to, ligand binding and crosslinking assays in which the HMVAB41 is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biohysical techniques such as surface plasmon resonance and spectroscopy. In addition to being used for purification and cloning of the receptor, these binding assays can be used to identify agonists and antagonists of HMVAB41 which compete with the binding of HMVAB41 to its receptors, if any. Standard methods for conducting screening assays are well understood in the art.

Examples of potential HMVAB41 polypeptide antagonists include antibodies or, in some cases, oligonucleotides or proteins which are closely related to the ligands, substrates, enzymes, receptors, etc., as the case may be, of the HMVAB41 polypeptide, e.g., a fragment of the ligands, substrates, enzymes, receptors, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for HMVAB41 polypeptides; or compounds which decrease or enhance the production of HMVAB41 polypeptides, which comprises:

(a) a HMVAB41 polypeptide, preferably that of SEQ ID NO:2;

(b) a recombinant cell expressing a HMVAB41 polypeptide, preferably that of SEQ ID NO:2;

(c) a cell membrane expressing a HMVAB41 polypeptide; preferably that of SEQ ID NO:2; or (d) antibody to a HMVAB41 polypeptide, preferably that of SEQ ID NO:2.

It will be appreciated that in any such kit, (a), (b), (c) or (d) may comprise a substantial component.

Prophylactic and Therapeutic Methods

This invention provides methods of treating abnormal conditions such as, cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections, related to both an excess of and insufficient amounts of HMVAB41 polypeptide activity.

If the activity of HMVAB41 polypeptide is in excess, several approaches are available. One approach comprises administering to a subject an inhibitor compound (antagonist) as hereinabove described along with a pharmaceutically acceptable carrier in an amount effective to inhibit the function of the HMVAB41 polypeptide, such as, for example, by blocking the binding of ligands, substrates, enzymes, receptors, etc., or by inhibiting a second signal, and thereby alleviating the abnormal condition. In another approach, soluble forms of HMVAB41 polypeptides still capable of binding the ligand, substrate, enzymes, receptors, etc. in competition with endogenous HMVAB41 polypeptide may be administered. Typical embodiments of such competitors comprise fragments of the HMVAB41 polypeptide.

In another approach, soluble forms of HMVAB41 polypeptides still capable of binding the ligand in competition with endogenous HMVAB41 polypeptide may be administered. Typical embodiments of such competitors comprise fragments of the HMVAB41 polypeptide.

In still another approach, expression of the gene encoding endogenous HMVAB41 polypeptide can be inhibited using expression blocking techniques. Known such techniques involve the use of antisense sequences, either internally generated or separately administered. See, for example, O'Connor, J Neurochem (1991) 56:560 in Oligodeoxvnucleotides as Antisense Inhibitors of Gene Expression, CRC Press, Boca Raton, Fla. (1988). Alternatively, oligonucleotides which form triple helices with the gene can be supplied. See, for example, Lee et al., Nucleic Acids Res (19 9) 6:3073; Cooney et al., Science (1988) 241:456; Dervan et al., Science (1991) 251:1360. The oligomers can be administered per se or the relevant oligomers can be expressed in vivo.

For treating abnormal conditions related to an underexpression of HMVAB41 and its activity, several approaches are also available. One approach comprises administering to a subject a therapeutically effective amount of a compound which activates HMVAB41 polypeptide, i.e., an agonist as described above, in combination with a pharmaceutically acceptable carrier, to thereby alleviate the abnormal condition. Alternatively, gene therapy may be employed to effect the endogenous production of HMVAB41 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996). Another approach is to administer a therapeutic amount of HMVAB41 polypeptides in combination with a suitable pharmaceutical carrier.

Formation and Administration

Peptides, such as the soluble form of HMVAB41 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expect to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

The cDNA clone, HMVAB41, was isolated from a human bone marrow stromal cell cDNA library. Expression of mRNA for HMVAB41 is rare in most cell types surveyed. The translated protein is predicted to have four short hydrophobic stretches; thus, it is likely to have a compact structure. The unusually high predicted isoelectric point (11.75) suggests that it may be involved in binding negatively charged molecules such as DNA; thus, one possible function is that it may act as a transcription factor.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide comprising a nucleotide sequence encoding a first polypeptide that has at least 97% identity over its entire length compared to the human HMVAB41 polypeptide as set forth in SEQ ID NO:2, or the complement of said nucleotide sequence, wherein % identity is equal to 100 (1–100n/103), wherein n is the total number of amino acids in the first polypeptide that are substituted, deleted or inserted compared to the polypeptide set forth as SEQ ID NO:2.

2. The isolated polynucleotide of claim 1, wherein said nucleotide sequence consists of the region of the polynucleotide as set forth in SEQ ID NO:1 that codes for the polypeptide as set forth in SEQ ID NO:2.

3. The isolated polynucleotide of claim 2, wherein said nucleotide sequence consists of the polynucleotide as set forth in SEQ ID NO:1.

4. The isolated polynucleotide of claim 1 which is DNA or RNA.

5. An expression vector comprising the isolated polynucleotide of claim 1 operably linked to a transcription promoter.

6. An isolated host cell comprising the vector of claim 5.

7. A process for producing an isolated host cell comprising the expression vector of claim 5, said process comprising either transforming or transfecting an isolated, compatible host cell with the expression vector of claim 5.

8. The isolated polynucleotide of claim 1 comprising a nucleotide sequence that codes for the human HMVAB41 polypeptide as set forth in SEQ ID NO:2.

9. An expression vector comprising the isolated polynucleotide of claim 8 operably linked to a transcription promoter.

10. An isolated host cell comprising the vector of claim 9.

11. A process for producing an isolated host cell that expresses human HMVAB41 polypeptide, said process comprising either transforming or transfecting an isolated, compatible host cell with the expression vector of claim 9.

12. A method for producing human HMVAB41 polypeptide comprising culturing the isolated host cell of claim 10 under conditions suitable for expression of the polynucleotide and production of said polypeptide, and then recovering the human HMVAB41 polypeptide from the culture.

* * * * *